United States Patent
Böhm et al.

(10) Patent No.: US 10,168,301 B2
(45) Date of Patent: Jan. 1, 2019

(54) METHOD AND DEVICE FOR DEFECT-SIZE EVALUATION

(71) Applicant: SIEMENS AKTIENGESELLSCHAFT, München (DE)

(72) Inventors: Rainer Böhm, Rietz-Neuendorf (DE); Karl Fendt, München (DE); Werner Heinrich, Oberkrämer OT Bärenklau (DE); Hubert Mooshofer, München (DE)

(73) Assignee: SIEMENS AKTIENGESELLSCHAFT (DE)

( * ) Notice: Subject to any disclaimer, the term of this patent is extended or adjusted under 35 U.S.C. 154(b) by 241 days.

(21) Appl. No.: 14/898,165

(22) PCT Filed: May 7, 2014

(86) PCT No.: PCT/EP2014/059318
§ 371 (c)(1),
(2) Date: Dec. 14, 2015

(87) PCT Pub. No.: WO2014/202275
PCT Pub. Date: Dec. 24, 2014

(65) Prior Publication Data
US 2016/0209371 A1    Jul. 21, 2016

(30) Foreign Application Priority Data
Jun. 20, 2013    (DE) .................. 10 2013 211 616

(51) Int. Cl.
*G01N 29/06* (2006.01)
*G01N 29/04* (2006.01)
*G01S 15/89* (2006.01)

(52) U.S. Cl.
CPC ......... *G01N 29/069* (2013.01); *G01N 29/043* (2013.01); *G01S 15/8997* (2013.01)

(58) Field of Classification Search
CPC .................................................... G01N 29/069
USPC .............................................. 73/606; 702/39
See application file for complete search history.

(56) References Cited

U.S. PATENT DOCUMENTS

| | | |
|---|---|---|
| 2007/0044561 A1 | 3/2007 | Engstrand et al. |
| 2008/0289423 A1 | 11/2008 | Gordon et al. |

FOREIGN PATENT DOCUMENTS

EP    2120045 A1    11/2009

OTHER PUBLICATIONS

Stepinski et al., "Synthetic aperture focusing techniques for ultrasonic imaging of solid objects," European Conference on Synthetic Aperture Radar (EUSAR), 2010.*

(Continued)

*Primary Examiner* — John Chapman, Jr.
(74) *Attorney, Agent, or Firm* — Schmeiser, Olsen & Watts LLP.

(57) ABSTRACT

A method and a device for defect-size evaluation of defects in a test object in ultrasonic testing is provided. In particular, the method and device also allows systematic determination of defect sizes based on the SAFT method. This is done by simulating defects in a test object on the basis of a defined test scenario, and comparing these simulations with actually recorded measured values.

20 Claims, 2 Drawing Sheets

(56) References Cited

OTHER PUBLICATIONS

Satyanarayan, L. et al "Simulation of ultrasonic phased array technique for imaging and sizing of defects using longitudinal waves"; in: International Journal of Pressure Vessels and Piping 84; pp: 716-729; 2007.
Schmitz, V. et al. "Calculation of high frequency ultrasonic signals for shear wave insonification in solid material"; in: Ultrasonics 42; pp. 2489-252; 2004.
Hunter, A.J. et al.. "The Wavenumber Algorithm for Full-Matrix Imaging Using an Ultrasonic Array", in: IEEE Transactions on Ultrasonics, Ferroelectrics and Frequency Control; vol. 55; No. 11; pp. 2450-2462; ; 2008.
Langenberg K. J. et al; "Imaging and Inverse Scattering in Nondestructive Evaluation with acoustic and Elastic Waves"; Acoustical Imaging, Nanjing, Sep. 12-14, 1992, Proceedings of the International Symposium on Acoustical Imaging, New York, Plenum Press; vol. 20; pp. 165-172; XP000448545; 1992.
McGarrity J. P. et al; "A Facet Ensemble Approach for Evaluation of Array Performance in Ultrasonic NDE"; IEEE Transactions on Ultrasonics, and Frequency Control; vol. 41; No. 1; pp. 19-25; ISSN: 0885-3010; DOI: 10.1109/58.265816; XP011439033; 1994.
International Search Report; PCT/EP2014/059318; 3 pgs.

\* cited by examiner

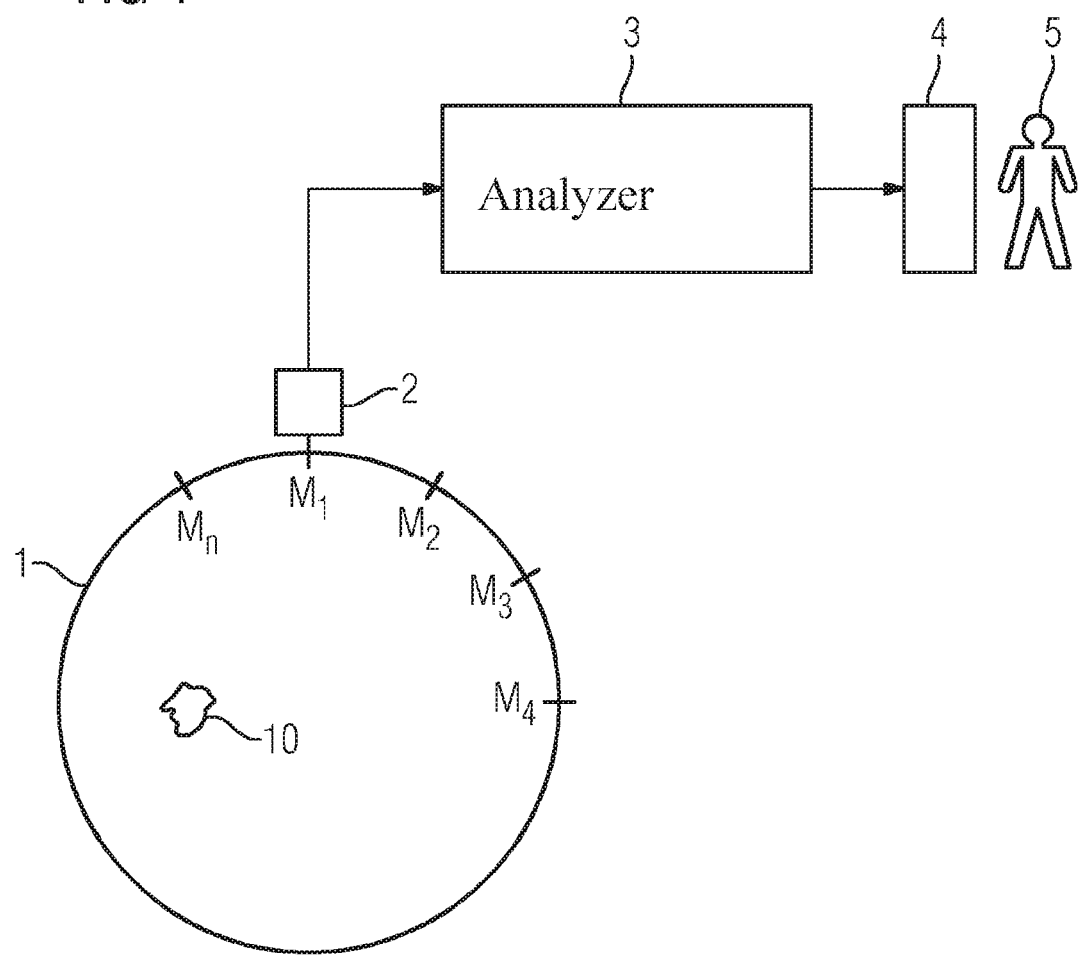

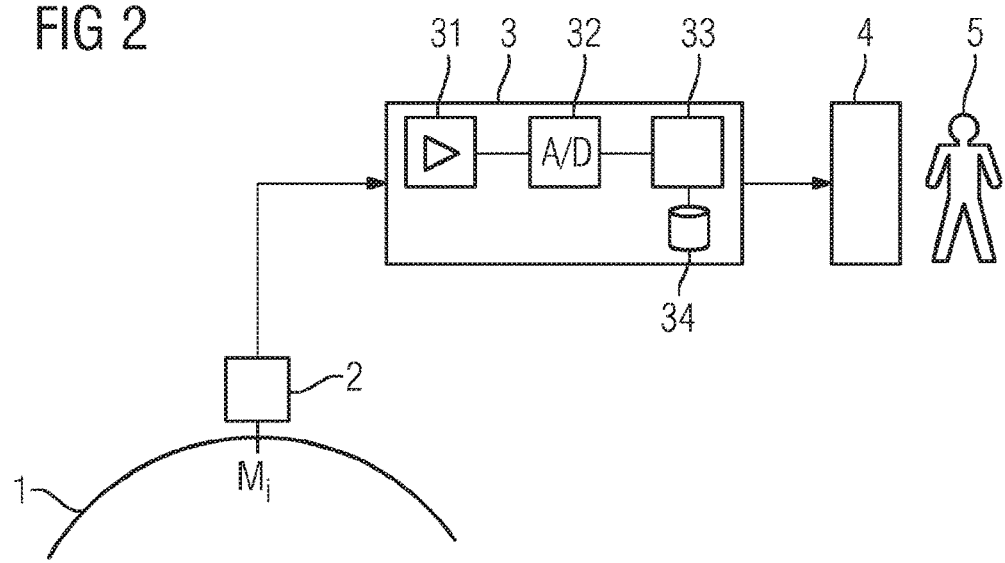
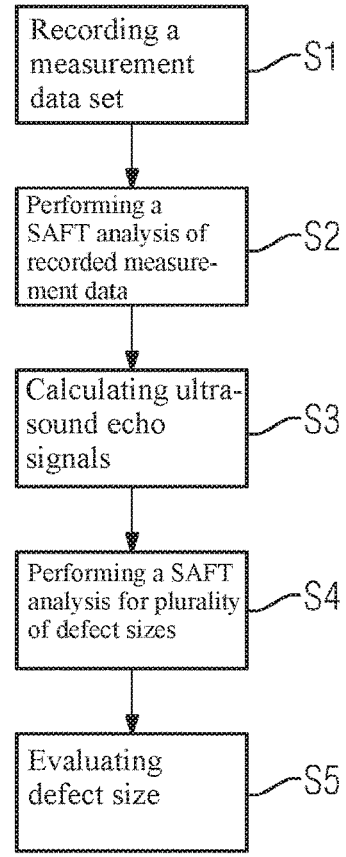

METHOD AND DEVICE FOR DEFECT-SIZE EVALUATION

CROSS-REFERENCE TO RELATED APPLICATIONS

This application claims priority to PCT Application No. PCT/EP2014/059318, having a filing date of May 7, 2014, based off of German Application No. 102013211616.0, having a filing date of Jun. 20, 2013, the entire contents of which are hereby incorporated by reference.

FIELD OF TECHNOLOGY

The following relates to a method and a device for defect-size evaluation of a defect inside a test object and in particular for defect-size evaluation of a defect by means of ultrasound.

BACKGROUND

Test objects, for instance machine components or the like, are tested after manufacture for the presence of defects such as small cavities or cracks, for example. Such a test is preferably performed using ultrasound. For such ultrasonic testing, the SAFT technique (Synthetic Aperture Focusing Technique) is known for detecting even very small defects inside the test object and for distinguishing said defects from other defects. The SAFT technique can be used to improve the lateral defect resolution, the defect demarcation and the SNR (signal-to-noise ratio) in ultrasonic testing.

Of key importance for assessing the test results is the evaluation of the size of defects, which forms the basis for determining the reliability. For defects that are large compared with the ultrasound wavelength used, measurements can be taken directly from the result of the SAFT analysis. Evaluating small defects, however, is only possible to a limited extent when using the SAFT technique.

In conventional ultrasonic testing, the reference block method and the DGS (Distance-Gain-Size) technique are known methods for evaluating the size of small defects. These methods determine from the maximum echo amplitude what is known as an "equivalent defect size", which is the size of an idealized reflector that would produce this maximum echo amplitude. In the reference block method, test defects are deliberately introduced at various distances from the measurement surface in a reference block that has the same ultrasonic properties as the test object, and an echo amplitude as a function of the sound path is determined therefrom. As an alternative to this, in the DGS method, the echo amplitude as a function of the sound path can be derived from a DGS diagram supplied by the test-head manufacturer.

Unlike conventional ultrasonic testing, the results of the SAFT technique are amplitude summations, i.e. summations of amplitude values of the ultrasound echoes. Depending on the test object, test grid (i.e. the arrangement of the measurement points on the test object) and test head, these amplitude summations are composed of different numbers of contributory elements, which may include echoes from signals in both central and side regions of the test-head sound beam. Thus the conventional methods for size evaluation of small defects cannot be applied to the SAFT technique.

Langenberg et al: "Imaging And Inverse Scattering In Nondestructive Evaluation With Acoustic And Elastic Waves", Acoustical Imaging, Nanjung, 12-14 Sep. 1992, Proceedings of the International Symposium on Acoustical Imaging, pages 165-172, discloses numerical modelling for simulating measurements, for example using SAFT analysis. The simulation methods presented are evaluated on the basis of existing measured values.

McGarrity et al: "A facet ensemble approach for evaluation of array performance in ultrasonic NDE", IEEE Transactions on Ultrasonics, Ferroelectrics and Frequency Control, Bd. 41, No. 1, 1 Jan. 1994, pages 19-24, ISSN: 0885-3010 discloses a simulation approach for evaluating the performance of arrays in nondestructive testing, in particular using SAFT analysis.

Document EP 2 147 300 A1 describes a modified SAFT technique in which the SAFT amplitude summations are calculated such that they can be compared with the conventional echo amplitude. In this case, however, the defects under inspection must not be too small, so that conventional amplitude evaluation is feasible. On the other hand, however, the defects must be small enough for the reflection not to be direction-dependent. Otherwise the defects would be underestimated.

SUMMARY

An aspect relates to a method and a device for defect-size evaluation of a defect inside a test object which avoids the aforementioned disadvantages and constraints and allows a widely useable evaluation of defect sizes of the order of the wavelength and below.

One idea of embodiments of the present invention is to calculate amplitude summations for defects of graduated sizes at representative defect positions by SAFT analysis of simulated ultrasound echo signals, and, by a comparison with the amplitude summations obtained from the SAFT analysis of the test data, to evaluate the size of such defects, which are small compared with the ultrasound wavelength used or are of the same order of magnitude.

The defect-size evaluation according to embodiments of the invention has the advantage that defects which would be lost in noise in conventional ultrasonic testing can now also be detected and evaluated.

Another advantage is that close adjacent defects can be evaluated as separate defects, for which hitherto only a joint evaluation was possible. Thus a material test using a defect-size evaluation according to embodiments of the invention provides more information about the material quality and allows testing and/or selection of components that must be designed for particularly high stresses, as is the case, for example, in turbine engineering, aviation or railways.

One possible embodiment of the invention also comprises a step for determining a defect position in the test object from the SAFT analysis of the recorded measurement-data set, wherein the step for calculating ultrasound echo signals calculates the ultrasound echo signals for a defect at the ascertained defect position in the test object.

This has the advantage that the calculation of simulated ultrasound echo signals and the subsequent SAFT analysis are confined to positions at which a defect is actually located in the test object.

In an alternative embodiment of the invention, the step for calculating ultrasound echo signals calculates the ultrasound echo signals for defects at a plurality of positions inside the test object, and performs a SAFT analysis of the calculated ultrasound echo signals for each calculated defect position.

If these simulations of the defects in the test object are performed already before the actual inspection of the test object, the computing time during object testing can be minimized.

In another possible embodiment of the invention, in the step for calculating ultrasound echo signals, the ultrasound echo signals are calculated for a test object having a plurality of defects inside the test object.

This has the advantage that the SAFT analysis of the calculated ultrasound signals is performed in one step.

In another embodiment of the invention, in the step for calculating ultrasound echo signals, the ultrasound echo signals are calculated for a plurality of test objects each having at least one defect.

In another possible embodiment of the invention, in order to evaluate the defect size, a position interpolation and/or a defect-size interpolation of the SAFT analyses of the calculated ultrasound echo signals is performed.

This has the advantage that very precise information about the defect size and/or defect position can be given on the basis of a relatively low number of simulated defects.

Another possible embodiment of the invention also comprises a step for providing parameters of a test scenario, wherein the step for calculating ultrasound echo signals is performed for a plurality of defect sizes in the test object using the provided parameters of the test scenario.

Such parameters for the test scenario may be, for example, the material or the geometry of the test object, a test grid or test-head parameters. Such parameters for the test scenario may be, for example, test-head parameters, specifications of a test grid, the material and/or the geometry of the test object.

This advantageously allows precise calculation of the ultrasound echo signals for each of the defects.

Another possible embodiment of the invention also comprises a step for providing external additional information about a defect inside the test object, wherein the step for evaluating a defect size evaluates the defect size using the external additional information provided.

For example, if additional data about the test object and/or the specific test setup is available, this data can advantageously also be incorporated in the test process, in particular in the defect-size evaluation.

In a specific embodiment, the additional information is information about the orientation of the defect in the test object.

In another possible embodiment of the invention, a plurality of measurement-data sets are recorded, and the SAFT analysis is performed using the plurality of recorded measurement-data sets.

The accuracy of the test can thereby be improved even more by this test of the test object using a plurality of individual measurement-data sets. For example, a plurality of measurement-data sets can be recorded using different incident beam angles.

In another possible embodiment of the invention, the analyzer also comprises a memory device, which is designed to store amplitude summations from the SAFT analysis of the calculated ultrasound echo signals, wherein the analyzer is designed to read out from the memory unit the stored amplitude summations for the calculated ultrasound echo signals and to adapt the read-out amplitude summations for the defect-size evaluation in the SAFT analysis of the recorded measurement-data set.

This has the advantage that the simulation results for defects from previous simulations can also be reused at this stage and adapted if applicable.

BRIEF DESCRIPTION

Some of the embodiments will be described in detail, with reference to the following figures, wherein like designations denote like members, wherein:

FIG. 1: is a diagram for explaining how the method and the device work for the defect-size evaluation according to an exemplary embodiment of the present invention;

FIG. 2: is a block diagram for illustrating an exemplary embodiment of the device for defect-size evaluation; and FIG. 3: is a flow diagram for illustrating an exemplary embodiment of the method for defect-size evaluation.

DETAILED DESCRIPTION

FIG. 1 shows schematically an exemplary embodiment of the device according to an embodiment of the invention for defect-size evaluation of a defect 10 inside a test object 1. In the example shown, the test object 1 has a cylindrical or rotationally symmetric design. Test objects 1 having a different geometry are also possible, however. The position of the test head 2 can be changed relative to the test object 1. This can be done, for instance, by moving the test head 2 along the surface of the test object 1. Alternatively, the test object 1 can be moved relative to the test head 2. The test head 2 thereby reaches different measurement points Mi. The test head 2 is used here to beam in an ultrasound signal at the various measurement points Mi of the test object 1. In order to record a measurement-data set, the ultrasound signal is beamed into the test object 1 at a specific incident beam angle for each recording. Different measurement-data sets can be recorded by varying the incident beam angle for each measurement-data set. The incident beam angle of the test head 2 can be varied, for instance, using wedges that are mounted between the test head 2 and the test object 1. In addition, the incident beam angle can also be varied by time-shifted control of the test head 2 if the test head 2 is an antenna array or the like. In principle it is also possible here to be able to use separate components for transmitting the ultrasound signals and receiving the echo signals instead of a test head 2 acting as both transmitter and receiver of the ultrasound signals. The recorded time signals are transmitted via a signal line to an analyzer 3. A display unit 4 for a tester 5 is connected, for example, to this analyzer 3.

The analyzer 3 performs a SAFT analysis (Synthetic Aperture Focusing Technique) for each recorded measurement-data set. The results of this SAFT analysis can then be displayed on the display device 4 after suitable preparation. For instance this preparation of the SAFT analysis includes the defect-size evaluation as explained in more detail below. In this process, it is also possible to record and analyze a plurality of measurement-data sets for a test object 1. All the SAFT analysis results from each of the measurement-data records are in this case preferably prepared on the basis of a common reconstruction grid.

If the test object 1 has a defect 10 that is relatively large compared with the wavelength used, then a measurement of the size of this defect 10 can be taken directly. For this purpose, for instance, a half-value method can be used to perform a size evaluation.

For relatively small defects, determining sizes by in this direct manner is not possible. There is no sharp transition point at which a direct defect-size evaluation is no longer possible. It does, however, become difficult to impossible particularly for defects of size less than or equal to the wavelength of the ultrasound frequency used. Therefore a defect-size evaluation of such small defects is performed by comparing simulation results with measured values. For this purpose, the analyzer 3 performs for different defects of graduated size and for different defect positions in the test object 1 a simulation of echo signals for the test scenario to be analyzed. For this purpose, the analyzer 3 receives as input parameters as detailed a specification as possible of the test scenario. This specification of the test scenario comprises, for example, parameters such as material and/or geometry of the test object 1, the test grid on which this measurement is based, and the known test-head parameters of the test head 2. Other available information and also any other additional information about the test object 1 and the general parameters of the test environment can also be incorporated in the simulation process.

The analyzer 3 performs a simulation of the echo signals on the basis of the information provided about the test scenario. In this simulation, the analyzer 3 calculates the possible ultrasound echo signals for different sizes and/or different positions of a defect 10 inside the test object 1. The simulations of the ultrasound echo signals can be calculated here using known conventional simulation techniques which are suitable for simulating in a suitable manner the sound propagation in the material of the test object 1, the characteristic of the test head 2 and the ultrasound reflection in the material. Such simulation techniques may be, for example, ray-based or grid-based techniques such as, for instance, point-source synthesis, the Elastodynamic Finite Integration Technique (EFIT) or the Finite Element (FE) method. Other simulation techniques that are suitable for calculating the ultrasound echo signals for a defect 10 inside the test object 1 in a suitable manner are also possible, however.

In this process, the analyzer 3 calculates for possible defects inside the test object 1 the ultrasound echo signals for defects 10 of different size. The defects 10 used for the basis of this calculation may be orientated in parallel with the surface, for example. Alternative orientations of the defects 10 are likewise possible, however. In addition, the geometry of the defects 10 on which the calculation is based can also be selected in a suitable manner. For instance it is possible to assume that the hypothetical defects are circular discs or spherical defects. Such circular or spherical defects as the basis for the simulation have the advantage that during the subsequent evaluation of the defect sizes, the particular defect size can be related to such standardized shapes as a circle or a sphere. It is also equally possible, however, for the defects on which the simulation is based to have any other geometry.

If the position of a defect 10 inside the test object 1 is already known in advance, then the calculation of the simulated ultrasound echo signals can also be narrowed by this already known defect position. The required computing time can hence be minimized. The defect position inside the test object 1 can be ascertained in advance by prior analysis of one or more measurement-data sets.

After the simulation of the ultrasound echo signals for different defect sizes, a SAFT analysis is performed on the calculated simulation results in the area around the defect positions. Then the maxim of the amplitude summations from the SAFT analysis in the area around the defect positions are ascertained. These amplitude summations of the simulation results for different defect sizes and, if applicable, different defect positions, are then arranged in an evaluation matrix. To reduce the computing time and the memory space required, the defect sizes and/or the defect positions can be graduated in a relatively coarse grid during the simulation. This means that during the calculation of the simulation results it is not necessary to perform a separate simulation of the ultrasound echo signals and subsequent SAFT analysis for every possible defect size and/or every possible grid position inside the test object 1. Instead, by suitable interpolation it is possible to achieve a finer graduation later. In principle any potential interpolation technique is possible for this purpose.

Linear interpolation between the individual defect positions is particularly applicable to the position interpolation of defects 10 inside the test object 1. In this case, linear interpolations in the dual-logarithmic scale and/or quadratic interpolations are particularly advantageous for interpolating the amplitude summations with regard to different defect sizes because these interpolations are particularly good at taking into account the typical dependencies between equivalent-defect size and amplitude summations in the case of two-dimensional equivalent defects. Yet even in this case other interpolation forms are also possible in principle. The amplitude summations which come from the SAFT analysis of the recorded measurement-data set are then analyzed using the SAFT analyses of the calculated ultrasound echo signals, for example using the generated evaluation matrix. Here, for the SAFT analysis of a recorded measurement-data record, the defect size and the defect position that come closest to the values in the evaluation matrix can be ascertained. Suitable interpolation can also be performed to obtain more precise results.

FIG. 2 shows an exemplary embodiment of the device according to embodiments of the invention for defect-size evaluation of a defect 10 inside a test object 1. In order to record a measurement-data set for the test object 1 by means of a test head 2, an ultrasound signal is beamed into the test object 1 at the measurement points Mi. The ultrasound echo signals reflected back by the test object 1 at the various measurement points Mi are detected by the test head 2 and transmitted to the analyzer 3 as a time signal for the particular measurement point Mi. The received ultrasound echo signal for the particular measurement point Mi is amplified by a signal amplifier 31 and digitized by an analog-to-digital converter 32 in the analyzer 3 into measurement-point echo data, which form the measurement-data set for the test object 1. The measurement-data set can then be analyzed and processed in a data processing unit 33, for example in a processor or the like. The data processing unit 33 performs a SAFT analysis for each measurement-data set. In addition, a calculation of the ultrasound echo signals inside the test object is performed in the data processing unit 33, in which calculation different defect sizes and, if applicable, also different defect positions are simulated. A SAFT analysis of the calculated ultrasound echo signals is performed, likewise in the data processing unit 33, on the basis of these simulated ultrasound echo signals. The amplitude summations obtained thereby in the SAFT analysis of the calculated ultrasound echo signals are arranged in an evaluation matrix.

Then detected smaller defects 10 inside the test object 1 are evaluated by the data processing unit 33 on the basis of a previously specified evaluation matrix, for example. The SAFT analysis and in particular the defect-size evaluation can then be displayed on a display device 4 for a user 5.

As already described, a defect position from the SAFT analysis of the measurement data can already be incorporated in the calculation of the simulation results. In order to reduce the delay caused by the large amount of simulation time during the analysis, the simulation and the generation of the evaluation matrix can also take place in advance. At this point in time, however, a definite defect position is still not known. In this case, therefore, the defect position inside the test object must also be varied during the simulation, and a simulation carried out for the different defect positions, because the reference size for evaluating the defect size depends on the position.

The computing time can be reduced here by storing in a memory device 34 an evaluation matrix already calculated in advance, and using this previously stored evaluation matrix repeatedly for subsequent analyses and evaluations of defect sizes.

If the test scenario should change slightly in a subsequent test, then a new refined or adapted evaluation matrix can still be generated using less computing time from a pre-generated evaluation matrix by means of suitable interpolation and/or by computational operations on the basis of the previously stored evaluation matrix. In particular, if there is a known formula relating various different test scenarios, then a new evaluation matrix for an adapted test scenario can be derived using less computing time from pre-generated evaluation matrices. For instance, if the test grid is made finer this results in a corresponding duplication of the amplitude summations.

In addition it is also possible in the SAFT analysis to weight differently the contributions from different measurement points. For instance a different weighting can be made according to the direction from the measurement point to the point to be analyzed. In this case, in the simulation, the contributions in the SAFT analysis are weighted in the same way as is done in the analysis of the measurement data.

It is possible, for instance, to perform a plurality of simulations of ultrasound echo signals for test objects that each have one defect, and then to analyze these simulations. Alternatively, however, it is equally possible to simulate a test object having a plurality of defects 10. In this case, however, a sufficient distance between the individual defects 10 must be guaranteed in order to prevent these defects 10 affecting one another. In addition, it is also possible to combine the two methods mentioned above. In this case, a plurality of test objects having a defined number of defects can each be simulated and analyzed separately.

FIG. 3 shows a flow diagram for illustrating an exemplary embodiment of the invention for defect-size evaluation of a defect 10 inside a test object 1.

In a step S1, a measurement-data set is first recorded for a test object 10.

In a further step S2, a SAFT analysis is performed for each recorded measurement-data set.

In addition, in step S3, a calculation of ultrasound echo signals is performed for a plurality of defect sizes in the test object 1. In this case, the defect size is varied in steps within a defined value range. Said defect sizes are preferably small compared with the ultrasound signal wavelength used or at least not much larger and therefore conventional means cannot be used to ascertain the size directly. Then in step S4, for the ultrasound echo signals calculated in step S3, a SAFT analysis is performed for all the calculated ultrasound echo signals for each of the defect sizes.

In step S5, an evaluation of the defect size is performed in the SAFT analysis of the recorded measurement-data set using the SAFT analysis of the calculated ultrasound echo signals. This evaluation of the defect sizes can be performed, for example, by comparing the SAFT analysis of the recorded measurement-data set with an amplitude summation of the individual SAFT analyses of the calculated ultrasound echo signals, which amplitude summation is tabled in an evaluation matrix. The equivalent-defect size can be ascertained on the basis of this evaluation. In the method according to embodiments of the invention, the advantages of the SAFT analysis also apply to very small defect sizes, because now a qualitative evaluation of smaller defects 10 is also possible. The defect-size evaluation according to embodiments of the invention of a defect 10 inside a test object 1 is likewise possible for evaluating defects having a directional or non-directional reflection. In addition, the defect-size evaluation according to embodiments of the invention is equally suitable for test heads having a small beam angle or even a large beam angle of the sound field.

An example of an ultrasound testing procedure using a defect-size evaluation according to embodiments of the invention may run as follows: a test object 1, for instance a safety-relevant component in turbine engineering, an aircraft or a railway, undergoes ultrasonic testing using a test head 2. For this purpose, the test head 2 is used to beam ultrasound waves into the test object 1 at various measurement points Mi, and the test head 2 detects the ultrasound echo signals from the test object 1. Frequencies of, for instance, 500 kHz to 20 MHz, preferably 2 MHz, are possible for the ultrasonic testing. In steel this corresponds to a wavelength of approximately 3 mm or approximately 1.6 mm.

The ultrasound echo signals are analyzed by the analyzer 3 using SAFT techniques, and displayed on the display device 4. If a defect 10 exists inside the test object 1, this defect can be detected by the analyzer 3 and visualized on the display device 4.

In order to be able to make a reliable estimate of the size even for small defects 10 for which a direct measurement can no longer be made because of the limited spatial resolution, the size is evaluated by comparing with simulation values. The data processing unit 33 in the analyzer 3 does this by performing a simulation for the defined test scenario (test object, test head, test grid etc.) for a plurality of defect sizes. If, for instance, the system cannot directly resolve defects of less than 3 mm, then calculations that simulate the ultrasound echo signals of commensurately small defects are performed for various defect sizes of less than 3 mm. In this process, the hypothetical defects 10 in the test object 1 can be graduated, for example linearly in steps of 0.5 mm or 0.2 mm. Then the data processing unit 33 performs a SAFT analysis of the calculated simulation values. If at the time of the calculation of the simulated defect the position of the defect is not known, then during the simulation of the defects 10 the position inside the test object must also be varied, and the defect size must be varied as described above for each of the different defect positions, because the reference size for the defect-size evaluation depends on the position.

An example of an evaluation matrix for a test object 1 having a cylindrical geometry is shown schematically in table 1 below. In this table, the rows correspond to different defect positions, and the columns to different defect sizes. The cells of the evaluation matrix each contain the amplitude summations from the calculated SAFT analysis.

TABLE 1

Example of an evaluation matrix

| Distance | Equivalent defect size | | |
|---|---|---|---|
| [mm] | 0.5 mm | 1.0 mm | 2.0 mm |
| 250 | 57.0 | 255.3 | 1025.9 |
| 300 | 55.2 | 247.3 | 992.9 |
| 350 | 54.7 | 244.8 | 981.5 |

TABLE 1-continued

Example of an evaluation matrix

| Distance | Equivalent defect size | | |
|---|---|---|---|
| [mm] | 0.5 mm | 1.0 mm | 2.0 mm |
| 400 | 53.8 | 240.8 | 962.9 |
| 450 | 53.2 | 237.7 | 947.0 |
| 500 | 52.5 | 234.6 | 928.8 |
| 550 | 51.6 | 229.7 | 899.3 |

The defect positions can be varied here for all possible grid points in the image plane of the SAFT analysis. To reduce the computing time, however, it is also possible to perform a simulation only for specific, selected defect positions. In this case, the exact defect position can be specified more precisely later, for instance, by interpolation.

Then the data processing unit 33 generates an evaluation matrix, in which are arranged the amplitude summations of the SAFT analyses for a plurality of defect sizes and, if applicable, also for different positions.

The simulation for the defect positions, i.e. the calculation of the ultrasound echo signals, the SAFT analysis of the calculated ultrasound echo signals and the generation of the evaluation matrix, can take place here already before the actual measurement of the test object 1. Thus only a small amount of processing power is needed during the test procedure. Since the defect position is still not known in this case during the simulation, it is imperative also to perform simulations for different defect positions.

Alternatively, the calculation of the ultrasound echo signals, the SAFT analysis of the calculated ultrasound echo signals and the generation of the evaluation matrix can also be performed only once a defect 10 has been detected in the test object. In this case, the simulation of the defects can be narrowed to the detected defect position. It is also possible in this case to use the existing measured values as a first approximation of a defect size. In this case, the simulation of the defect size can be restricted to sizes in the region of the estimated value. For instance, if the measurement result suggests that the defect has a size in the region of 1 mm, for example, then the simulation can be restricted to defect sizes in the range of 0.5 mm to 2 mm, thereby further reducing the computing power required.

Once the SAFT analysis of the measured values and the evaluation matrix are available, a comparison is carried out. This comparison determines that value in the evaluation matrix that comes closest to the measured values. The actual defect size and, if applicable, defect position can then be deduced therefrom.

In addition, by interpolating adjacent values of the evaluation matrix, it is possible to obtain an even closer approximation for the estimated defect size and defect position.

Once the size and, if applicable, the position of a defect 10 has been ascertained in the manner described above, the ascertained values are displayed to the user on the display device 4.

By a defect-size evaluation according to embodiments of the invention, a direct comparison between conventional ultrasound analysis techniques and SAFT-based ultrasound techniques is now also possible. Any defects can be compared using the circular disc as the equivalent defect type. It is thereby possible, for instance, to make a differentiated comparison with the stresses in the design. The simulation of the ultrasound echo signals can also take into account that for very small circular discs, the echo level is no longer proportional to $d^2$, where d is the diameter of the equivalent defect size. Thus even these cases can be evaluated correctly. Furthermore, the method according to embodiments of the invention also allows further additional information about a defect 10 to be taken into account. Thus, for instance, orientations of defects can be taken into account by using for the evaluation a series of defects of graduated size having the known orientation.

To summarize, embodiments of the present invention relates to a defect-size evaluation of defects 10 in a test object 1 in ultrasonic testing. Embodiments of the present invention, in particular, also allow systematic determination of defect sizes based on the SAFT method. This is done by simulating defects 10 in a test object 1 on the basis of a defined test scenario, and comparing these simulations with actually recorded measured values.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method for defect-size evaluation of a defect in a test object, comprising the steps:
    recording a measurement-data set of a defect in the test object using actual ultrasound echo signals, wherein the measurement-data set includes a defect size of the defect, and wherein the defect size of the defect is smaller than a wavelength of the actual ultrasound echo signals;
    performing a Synthetic Aperture Focusing Technique, SAFT, analysis of the recorded measurement-data set;
    generating a plurality of possible defects in the test object, wherein each of the possible defects has a defect size;
    calculating ultrasound echo signals for the defect sizes of the plurality of possible defects in the test object by simulating echo signals for a test scenario;
    performing a SAFT analysis for the calculated ultrasound echo signals for each of the defect sizes of the plurality of possible defects;
    evaluating the defect size of the defect by comparing the SAFT analysis of the recorded measurement-data with the SAFT analyses of the calculated ultrasound echo signals, wherein the step of comparing the SAFT analysis of the recorded measurement-data with the SAFT analyses of the calculated ultrasound echo signals comprises arranging an amplitude summation of each SAFT analysis of the calculated ultrasound echo signals in an evaluation matrix and comparing an amplitude summation of the SAFT analysis of the recorded measurement-data with the evaluation matrix.

2. The method as claimed in claim 1, also comprising a step for determining a defect position in the test object from the SAFT analysis of the recorded measurement-data set, wherein the step for calculating ultrasound echo signals calculates the ultrasound echo signals for a defect at the ascertained defect position in the test object.

3. The method as claimed in claim 1, wherein the step for calculating ultrasound echo signals calculates the ultrasound echo signals for defects at a plurality of positions inside the test object, and performs a SAFT analysis of the calculated ultrasound echo signals for each calculated defect position.

4. The method as claimed in claim 1, wherein the step for calculating ultrasound echo signals calculates the ultrasound echo signals for a test object having a plurality of defects inside the test object.

5. The method as claimed in claim 1, wherein the step for calculating ultrasound echo signals calculates the ultrasound echo signals for a plurality of test objects each having at least one defect.

6. The method as claimed in claim 1, wherein the SAFT analyses of the calculated ultrasound echo signals are performed for a plurality of test objects each having at least one defect.

7. The method as claimed in claim 1, wherein the step for the evaluation comprises a position interpolation and/or a defect-size interpolation of the SAFT analyses of the calculated ultrasound echo signals.

8. The method as claimed in claim 1, further comprising a step for calculating ultrasound echo signals for a plurality of defect sizes in the test object using provided parameters of the test scenario.

9. The method as claimed in claim 8, wherein the provided parameters of the test scenario comprise information about test-head parameters, a test grid, material and/or geometry of the test object.

10. The method as claimed in claim 1, further comprising a step for providing information about a defect inside the test object, wherein the step for evaluating a defect size evaluates the defect size using the information provided.

11. The method as claimed in claim 10, wherein the external additional information provided comprises information about an orientation of the defect in the test object.

12. The method as claimed in claim 1, wherein a plurality of measurement-data sets are recorded, and the SAFT analysis is performed using the plurality of recorded measurement-data sets.

13. The method as claimed in claim 12, wherein to record the plurality of measurement-data sets an actual ultrasound signal is beamed into the test object at different measurement points at an incident beam angle that is varied for each measurement-data set in order to determine the plurality of measurement-data sets.

14. The method as claimed in claim 1, wherein the evaluated defect size is less than 3 mm.

15. The method as claimed in claim 1, wherein the step of calculating ultrasound echo signals for a plurality of defect sizes is graduated linearly in steps of 0.5 mm or 0.2 mm.

16. The method as claimed in claim 1, wherein a position of the defect in the test object is ascertained in advance.

17. A device for defect-size evaluation of a defect inside a test object, comprising:
a test head for beaming an actual ultrasound echo signal into the test object at different measurement points in order to determine at least one measurement-data set, and
an analyzer, which is designed to perform a Synthetic Aperture Focusing Technique, SAFT, analysis of the recorded measurement-data set, to calculate ultrasound echo signals for a plurality of defect sizes in the test object by simulating echo signals for a test scenario, to perform a SAFT analysis for the calculated ultrasound echo signals for each of the plurality of defect sizes, and to evaluate a defect size in the SAFT analysis of the recorded measurement-data set by comparing with the SAFT analyses of the calculated ultrasound echo signals, wherein the analyzer also comprises a memory device, which is designed to store amplitude summations from the SAFT analysis for the calculated ultrasound echo signals, and wherein the analyzer is designed to read out from the memory unit the stored amplitude summations for the calculated ultrasound echo signals and to adapt the read-out amplitude summations for the defect-size evaluation in the SAFT analysis of the recorded measurement-data set.

18. The device of claim 17, wherein the defect sizes evaluated are smaller than a wavelength of the actual ultrasound echo signals.

19. The device as claimed in claim 18, wherein the measurement data set detects defect sizes less than 3 mm.

20. The device as claimed in claim 17, wherein calculated ultrasound echo signals for a plurality of defect sizes is graduated linearly in steps of 0.5 mm or 0.2 mm.

* * * * *